US011432947B2

(12) United States Patent
Zahedi et al.

(10) Patent No.: US 11,432,947 B2
(45) Date of Patent: Sep. 6, 2022

(54) LOWER LIMB PROSTHESIS

(71) Applicant: BLATCHFORD PRODUCTS LIMITED, Hampshire (GB)

(72) Inventors: Mir Saeed Zahedi, London (GB); Graham Harris, Hampshire (GB); Stephen Terry Lang, Hampshire (GB); Robert Michael Andrew Painter, Wokingham (GB); David Moser, Hampshire (GB)

(73) Assignee: Blatchford Products Limited, Hampshire (GB)

( * ) Notice: Subject to any disclaimer, the term of this patent is extended or adjusted under 35 U.S.C. 154(b) by 0 days.

(21) Appl. No.: 16/026,110

(22) Filed: Jul. 3, 2018

(65) Prior Publication Data

US 2019/0046336 A1  Feb. 14, 2019

Related U.S. Application Data

(63) Continuation of application No. 14/416,509, filed as application No. PCT/GB2013/051963 on Jul. 23, 2013, now Pat. No. 10,039,652.

(Continued)

(30) Foreign Application Priority Data

Jul. 23, 2012 (GB) .................................... 1213035

(51) Int. Cl.
*A61F 2/70* (2006.01)
*A61F 2/64* (2006.01)
(Continued)

(52) U.S. Cl.
CPC .................. *A61F 2/70* (2013.01); *A61F 2/60* (2013.01); *A61F 2/64* (2013.01); *A61F 2/6607* (2013.01);
(Continued)

(58) Field of Classification Search
CPC ................................................... A61F 2002/74
See application file for complete search history.

(56) References Cited

U.S. PATENT DOCUMENTS

| 5,121,747 A | * | 6/1992 | Andrews | ............ | A61N 1/36003 |
|---|---|---|---|---|---|
| | | | | | 602/16 |
| 6,033,440 A | * | 3/2000 | Schall | ...................... | A61F 2/76 |
| | | | | | 403/84 |

(Continued)

FOREIGN PATENT DOCUMENTS

| DE | 102008045113 | 3/2010 |
|---|---|---|
| WO | WO 99/08621 | 2/1999 |

(Continued)

OTHER PUBLICATIONS

International Search Report and Written Opinion for International Application No. PCT/GB2013/051963, dated Oct. 25, 2013.

(Continued)

*Primary Examiner* — Jacqueline Woznicki
(74) *Attorney, Agent, or Firm* — Alston & Bird LLP (57) ABSTRACT

A prosthetic ankle has an ankle joint body (10A) constituting a shin component and a foot component (12). The ankle joint body (10A) is pivotally connected to the foot component (12) by a first pivotal connection (14) defining a medial-lateral ankle joint flexion axis. The ankle joint body (10A) also forms the cylinder of an ankle joint piston and cylinder assembly with a superior-inferior central axis, the cylinder housing a piston (16) with upper and lower piston rods (16A, 16B). The lower piston rod (16B) is pivotally connected to the foot component (12) at a second pivotal connection (18). As the ankle joint body (10A) pivots about the ankle joint flexion axis, the piston (16) moves substantially linearly in the cylinder formed by the ankle joint body. The cylinder is divided into upper and lower chambers (20A, 20B). These chambers are linked by an hydraulic circuit (22) incorpo- (Continued)

rating passages (22A, 22B) in the ankle joint body (10A), and an energy conversion device in the form of a slave piston and cylinder assembly (24) having a piston (24P) and piston rods (24R) which project beyond the cylinder (24C) of the assembly (24).

17 Claims, 6 Drawing Sheets

Related U.S. Application Data (60) Provisional application No. 61/675,347, filed on Jul. 25, 2012.

(51) Int. Cl.
| | | |
|---|---|---|
| *A61F 2/66* | (2006.01) | |
| *A61F 2/68* | (2006.01) | |
| *A61F 2/74* | (2006.01) | |
| *A61F 2/50* | (2006.01) | |
| *A61F 2/60* | (2006.01) | |
| *A61F 2/76* | (2006.01) | |

(52) U.S. Cl.
CPC ............... *A61F 2/74* (2021.08); *A61F 2/741* (2021.08); *A61F 2/748* (2021.08); *A61F 2002/5006* (2013.01); *A61F 2002/5032* (2013.01); *A61F 2002/5072* (2013.01); *A61F 2002/5079* (2013.01); *A61F 2002/607* (2013.01); *A61F 2002/6678* (2013.01); *A61F 2002/6818* (2013.01); *A61F 2002/704* (2013.01); *A61F 2002/7615* (2013.01)

(56) References Cited

U.S. PATENT DOCUMENTS

| | | | | |
|---|---|---|---|---|
| 6,113,642 | A * | 9/2000 | Petrofsky | A61F 2/68 |
| | | | | 188/282.3 |
| 6,443,993 | B1 | 9/2002 | Koniuk | |
| 8,698,329 | B2 | 4/2014 | Loverich et al. | |
| 8,764,850 | B2 * | 7/2014 | Hansen | A61F 2/70 |
| | | | | 623/47 |
| 8,928,161 | B2 | 1/2015 | Loverich et al. | |
| 2002/0138153 | A1 * | 9/2002 | Koniuk | A61F 2/6607 |
| | | | | 623/24 |
| 2004/0054423 | A1 * | 3/2004 | Martin | A61F 2/6607 |
| | | | | 623/25 |
| 2004/0064195 | A1 * | 4/2004 | Herr | A61F 2/66 |
| | | | | 623/24 |
| 2004/0186590 | A1 | 9/2004 | Townsend et al. | |
| 2005/0192677 | A1 | 9/2005 | Ragnarsdottir et al. | |
| 2006/0235544 | A1 * | 10/2006 | Iversen | A61F 2/64 |
| | | | | 623/26 |
| 2006/0249315 | A1 | 11/2006 | Herr et al. | |
| 2007/0050044 | A1 | 3/2007 | Haynes et al. | |
| 2007/0213840 | A1 * | 9/2007 | Townsend | A61F 2/60 |
| | | | | 623/51 |
| 2007/0233279 | A1 | 10/2007 | Kazerooni et al. | |
| 2008/0262635 | A1 * | 10/2008 | Moser | A61F 2/68 |
| | | | | 623/47 |
| 2009/0054996 | A1 | 2/2009 | Sykes et al. | |
| 2009/0222105 | A1 | 9/2009 | Clausen | |
| 2009/0260426 | A1 * | 10/2009 | Lieberman | A61B 5/1036 |
| | | | | 73/65.01 |
| 2009/0265018 | A1 * | 10/2009 | Goldfarb | A61F 2/72 |
| | | | | 623/40 |
| 2009/0299489 | A1 * | 12/2009 | Gramnaes | A61F 2/60 |
| | | | | 623/27 |
| 2010/0286796 | A1 * | 11/2010 | Clausen | A61F 2/64 |
| | | | | 623/39 |
| 2011/0098828 | A1 * | 4/2011 | Balboni | A61F 2/60 |
| | | | | 623/40 |
| 2011/0224804 | A1 * | 9/2011 | Clausen | A61F 2/68 |
| | | | | 623/47 |
| 2011/0230975 | A1 | 9/2011 | Moser et al. | |
| 2012/0330439 | A1 * | 12/2012 | Goldfarb | A61F 2/60 |
| | | | | 623/24 |
| 2013/0024006 | A1 | 1/2013 | Balli et al. | |
| 2013/0317627 | A1 | 11/2013 | Loverich et al. | |
| 2015/0320573 | A1 * | 11/2015 | Gramnaes | A61F 2/68 |
| | | | | 623/26 |
| 2016/0074180 | A1 * | 3/2016 | Lenzi | A61F 2/70 |
| | | | | 623/24 |
| 2016/0242936 | A1 * | 8/2016 | Goldfarb | A61F 2/68 |
| 2018/0036148 | A1 * | 2/2018 | Lincoln | A61B 5/4851 |

FOREIGN PATENT DOCUMENTS

| | | |
|---|---|---|
| WO | WO2006/024876 | 3/2006 |
| WO | WO 2007/110585 | 10/2007 |
| WO | WO 2008/103917 | 8/2008 |
| WO | WO 2012/151515 | 11/2012 |
| WO | WO 2013/088142 | 6/2013 |

OTHER PUBLICATIONS

Extended European Search Report for EP20156567.8 dated Jul. 6, 2020 (7 pages).

* cited by examiner

FUNCTIONS

| TASK | Initial stance | | ankle control | knee control | Midstance | | ankle control | knee control | Terminal stance | | ankle control | knee control |
|---|---|---|---|---|---|---|---|---|---|---|---|---|
| | ANKLE/FOOT | KNEE | | | ANKLE/FOOT | KNEE | | | ANKLE/FOOT | KNEE | | |
| Slow walk | LD-PF Er | HD, kflx, ER | | | MD DF ER | Pwr kext | | | none | Pwr kflx | | |
| Normal Walk | MD-PF Er | HD, kflx, ER | | | LD DF | Pwr kext | | | none | Pwr kflx | | |
| | | | D, A into X, or Z into | | | | | | | | | |
| fast Walk | HD-PF Er | HD, kflx, ER | acc | acc | Pwr DF | Pwr kext | B & E | Z | Pwr PF | Pwr kflx | D & B | Y |
| Up Hill | HD-PF Er | HD, kflx, ER | | | Pwr DF | Pwr kext | | | Pwr PF | Pwr kflx | | |
| Down Hill | LD-PF Er | HD, kflx, ER | | | HD DF ER | MD Kext | | | none | MD kflx | | |

| TASK | Initial Swing | | ankle control | knee control | Mid Swing | | ankle control | knee control | Terminal Swing | | knee control |
|---|---|---|---|---|---|---|---|---|---|---|---|
| | ANKLE/FOOT | KNEE | | | ANKLE/FOOT | KNEE | | | ANKLE/FOOT | KNEE | |
| Slow walk | DF to neutral | LD kflx, ER | | | none | LD Kext | | | none | HD Kext, ER | |
| Normal Walk | DF to neutral | MD kflx, ER | | | none | MD Kext | | | none | HD Kext, ER | |
| fast Walk | DF to neutral | MD kflx, ER | B & E | X | none | Pwr kext | | Z | none | HD Kext, ER | X |
| Up Hill | none | MD kflx, ER | | | none | Pwr kext | | | none | HD Kext, ER | |
| Down Hill | DF to neutral | MD kflx, ER | | | none | MD Kext | | | none | HD Kext, ER | |

LD = Low Damping
MD = Medium Damping
HD = High Damping
DF = dorsiflexion
PF = plantarflexion
Kext = Knee extension
kflx = Knee flexion
Pwwr = Power burst
ER = energy recovery

LOWER LIMB PROSTHESIS

CROSS-REFERENCE TO RELATED APPLICATIONS

This application is a continuation of U.S. application Ser. No. 14/416,509, filed Jan. 22, 2015, which application is a U.S. national phase under 35 U.S.C. § 371 of International Application PCT/GB2013/051963, filed Jul. 23, 2013, which claims priority to U.S. Provisional Application No. 61/675,347, filed Jul. 25, 2012, and United Kingdom Application No. GB 1213035.7, filed Jul. 23, 2012, each of which is incorporated herein in its entirety by reference.

This invention relates to a lower limb prosthesis having interconnected load-bearing structural members which are movable relative to each other when the prosthesis is loaded. A processor-controlled movement control device controls the relative movement in response to signals received from a sensor or sensors for sensing a kinetic or kinematic parameter of locomotion.

Known lower limb prostheses include those with adaptive control systems for controlling knee flexion or ankle flexion during both stance and swing phases of the walking gait cycle. In WO 99/08621, a prosthetic knee joint has a knee flexion control device including hydraulic and pneumatic parts for controlling knee flexion during the stance phase and swing phase of the gait cycle respectively, the control system including sensors for sensing shin bending moment and knee flexion angle, with corresponding electrical signals being fed to a processing circuit for automatically adjusting the hydraulic and pneumatic flexion control elements. Knee flexion is controlled in the stance phase in response to the activity mode of the amputee, i.e. in response to changes between level walking, walking uphill, and walking downhill, and in the swing phase in response to walking speed. The disclosure of WO 99/08621 is incorporated herein by reference. Dynamically variable damping of a prosthetic ankle joint is described in, for example, WO 2008/103917 and related U.S. application Ser. No. 13/150,694 filed 1 Jun. 2011 and published as US 2011/0230975, the disclosure of which is incorporated herein by reference. In this example, the ankle joint includes an hydraulic piston and cylinder assembly providing independent variation of damping resistance in dorsi-flexion and plantar-flexion directions in response to, e.g., ground inclination.

PCT Patent Application published as WO 2013/088142, which claims priority from British Patent Application No. 1208410.9, filed 14 May 2012, abandoned British Patent Application No. 1121437.6, filed 13 Dec. 2011 as well as corresponding U.S. Provisional Patent Applications Nos. 61/580,887 and 61/647,016, filed 28 Dec. 2011 and 15 May 2012 respectively, discloses an integrated lower limb prosthesis for a transfemoral amputee which is integrated in the sense that both knee and ankle joints are controlled, each joint being dynamically adjustable by a processor in response signals received at different levels in the prosthesis in response to, for instance, to signals at the level of the foot or ankle and at a higher level, e.g., on a shin member or at the knee. The disclosure of these applications is incorporated in the present application by reference.

Such an electronically controlled prosthesis can include "self-teaching" functions whereby, for instance, the processor can be set to a teaching mode in which data is gathered from sensors on the limb when the amputee performs a walking trial and the data is used to generate a range of settings automatically for use in a normal walking mode. A prosthesis having these features is disclosed in WO 2007/110585 and corresponding U.S. patent application Ser. No. 12/282,541 and published as US 2009/0057996, filed 11 Sep. 2008. The disclosure of this document is also incorporated herein by reference.

All of the above prostheses are passive in the sense that their respective control systems vary the resistance in the knee joint or ankle joint, as the case may be, to suit the amputee and the particular actions being performed at any given time. Walking is powered entirely by the muscle power of the amputee. A powered prosthesis is known, i.e. a prosthesis in which the amputee's own muscle power is supplemented with power supplied from an energy source within the prosthesis, in particular from a rechargeable battery. Rotation of the knee joint or ankle joint is driven by one or more actuators powered from the battery. Such prostheses require large batteries and frequent recharging. They also tend to be noisy.

WO 2012/151515 to The Cleveland Clinic Foundation discloses an energy-storing prosthetic knee.

DE 102008045113 to Bock Healthcare GmbH describes an orthopaedic arrangement for use as a prosthesic device for insertion at a lower extremity.

US 2006/0249315 to Massachusetts Institute of Technology describes an artificial human limb and joints employing actuators, springs, and variable-damper elements.

US 2009/0222105 to Ossur hf describes a transfemoral prosthetic system and method for operating the same.

US 2005/0192677 to Ossur hf describes a system and method for controlling the motion of a foot.

It is an object of the present invention to provide an improved powered prosthesis.

According to a first aspect of the invention, there is provided a lower limb prosthesis as recited in claim 1 hereinafter. In one embodiment of the invention the first and second structural members are integrally formed as a curved monolithic leaf spring, the movement control device comprising an hydraulic ram interconnecting the two members. In another embodiment the prosthesis comprises a pivotal joint which includes an upper component, a lower component pivotally mounted to the upper component, and a flexion control system for controlling relative pivoting movement between the upper component and the lower component, wherein the flexion control system comprises: an hydraulic circuit including an hydraulic joint flexion control device interconnecting the upper and lower components, and an energy conversion device for converting fluid flow energy in the hydraulic circuit resulting from joint flexion into mechanical movement and vice versa; an energy storage element arranged to store energy from the said energy conversion device and to feed stored energy back to the energy conversion device to cause fluid flow in the hydraulic circuit thereby to generate a joint flexion moment; and an energy input arranged to receive energy into the flexion control system from an external energy source; and wherein the prosthesis further comprises at least one sensor for sensing a kinetic or kinematic parameter of locomotion and a processor coupled to the sensor and the flexion control system and arranged to control both the storage of energy associated with fluid flow resulting from flexion of the joint and the delivery of energy to drive flexion of the joint at different parts of a walking gait cycle in response to signals received from the sensor or sensors. The ability to store energy using fluid flow in the hydraulic circuit resulting from joint flexion and to deliver energy to the joint via the hydraulic circuit at different parts of the walking gait cycle allows construction of a prosthesis which is relatively energy efficient and quiet in operation. The preferred energy storage element is a rechargeable battery and, in this case, the flexion control system preferably includes an electrical machine operable, firstly, as a generator to convert the mechanical energy produced by the above-mentioned energy conversion device into electrical energy for charging the battery and, secondly, as a motor to feed stored electrical energy from the battery to the energy conversion device. In this case, the energy input referred to above can be coupled to the battery to charge the battery from the external energy source.

The energy conversion device may comprise a piston and cylinder assembly in the hydraulic circuit, together with a gear mechanism for converting linear motion to rotary motion, the preferred electrical machine being a rotary machine.

Alternatively, the energy conversion device may comprise a turbine in the hydraulic circuit, the turbine being coupled to the electrical machine.

The energy storage element may form at least part of a pressure accumulator comprising, for instance, the combination of a pressure vessel having a variable-volume chamber for hydraulic fluid, the chamber being bounded by a movable piston which is spring loaded. In this case, the hydraulic circuit is typically arranged to cause pressure within the pressure vessel to be increased as fluid is driven around the hydraulic circuit by joint flexion. In response to the increase in pressure, the piston moves and the spring is compressed, thereby storing the fluid flow energy resulting from joint flexion. It is possible to have an accumulator in which the spring bears against a movable spring base, the spring base being connected to an electrical motor by a gear mechanism. In this way, the motor can be used to increase or decrease the fluid pressure in the accumulator as a way of increasing the energy in the flexion control system from another energy source, e.g. a battery connected to the motor.

In general, an electrical machine associated with the energy conversion device or an accumulator can be used to vary the resistance to fluid flow in the hydraulic circuit so that the energy conversion device can be used not only as a means of powering joint flexion but also as a means of controlling the resistance to joint flexion produced by the application of the amputee's weight to the prosthesis during walking or other activities.

In the preferred prosthesis, the flexion control system and the processor are arranged such that the joint flexion control device is driven to apply a joint flexion moment in at least one selected part of the gait cycle in response to signals received from the sensor or sensors and such that, in the other parts of the gait cycle, the joint flexion control device is operated passively to drive fluid in the hydraulic circuit, preferably to cause energy to be stored in the energy storage element. In the case of the pivotal joint being an ankle joint, the selected part of the gait cycle may comprise a final part of the stance phase, at which time the joint flexion device, in this case an ankle flexion control device, is driven to urge the foot component in the direction of plantar-flexion so as to assist forward acceleration at toe-off. Additionally, or as an alternative, the ankle flexion control device is driven during a mid-stance part of the stance phase to urge the foot component in the direction of dorsi-flexion, helping to urge the centre of gravity of the amputee forwardly during the stance phase.

In the case of the pivotal joint being a knee joint, the joint flexion control device being a knee flexion control device, the latter is driven to urge a lower knee component relative to an upper knee component (a) in the direction of knee extension in a mid-stance part of the gait cycle stance phase, (b) in the direction of knee flexion in a final part of the gait cycle stance phase, and/or (c) in the direction of knee extension in a mid-swing part of the gait cycle swing phase. Passive operation of the knee flexion control device to drive fluid in the hydraulic circuit and thereby to cause energy to be stored in the energy storage element preferably occurs (a) in an initial part of the gait cycle stance phase, (b) in an initial part of the gait cycle swing phase, and/or (c) in a final part of the gait cycle swing phase.

According to a second aspect of the invention, a prosthetic ankle comprises a shin component, a foot component pivotally mounted to the shin component, and a flexion control system for controlling relative pivoting movement between the shin component and the foot component, wherein the flexion control system comprises: an hydraulic circuit including an hydraulic ankle flexion control device interconnecting the shin and foot components, and an energy conversion device for converting fluid flow energy in the hydraulic circuit resulting from ankle flexion into mechanical movement and vice versa; an energy storage element arranged to store energy from the said energy conversion device and to feed stored energy back to the energy conversion device to cause fluid flow in the hydraulic circuit thereby to generate an ankle flexion moment; and an energy input arranged to receive energy into the flexion control system from an external energy source; and wherein the prosthetic ankle further comprises at least one sensor for sensing a kinetic or kinematic parameter of locomotion and a processor coupled to the sensor and the flexion control system and arranged to control both the storage of energy associated with fluid flow resulting from ankle flexion and the delivery of energy to drive ankle flexion at different parts of a walking gait cycle in response to signals received from the sensor or sensors.

The above-described prosthetic ankle may form part of a lower limb prosthesis for a transfemoral amputee or an amputee with a through-knee disarticulation. The prosthesis includes, in addition to the prosthetic ankle, a prosthetic knee, a shin member interconnecting the ankle and the knee, and a prosthetic foot, wherein the prosthetic knee comprises an upper knee component for connection to the residual limb of the amputee, a lower knee component associated with the shin member and pivotally mounted to the upper component, and an hydraulic knee flexion control device interconnecting the upper and lower knee components. The knee flexion control device, in this case, forms part of the hydraulic circuit including the ankle flexion control device. The knee joint and the ankle joint may share not only a common hydraulic circuit but also a common energy storage element. Thus, the flexion control system and the processor may be arranged such that fluid flow energy in the hydraulic circuit resulting from knee flexion is converted in the above-mentioned energy conversion device to a mechanical movement, energy associated with such movement being stored in the above-mentioned energy storage element, and such that energy stored in the energy storage element and converted back to fluid flow energy may be directed to the knee flexion control device to generate a knee flexion moment in a manner similarly to the above-described direction of fluid flow energy to the ankle flexion control device. It follows, also, that stored energy resulting from flexion of one joint can be returned to power flexion of the other joint.

In addition to embodiments of this invention having a flexion control system for controlling flexion of ankle and knee joints, the invention can also be used to assist flexion of hip joints. This assistance may be provided in the form on an orthosis applied to the hip of an amputee. The flexion control device can then be used to assist the amputee to raise his or her upper leg, for example when walking up stairs or up a slope, where an increased amount of hip flexion is required compared to when walking on a flat surface.

References to "flexion", "flexion control" and "powering flexion" in this specification are to be interpreted in the general sense of including the movement of, the control of and the powering of flexion and/or extension (rather than merely in the sense of increasing bending of the joint).

According to a third aspect of the invention, a lower limb prosthesis for a transfemoral amputee or an amputee with a knee disarticulation comprises a mounting portion, a knee joint, a shin member, an ankle joint and a foot member, wherein (i) the knee joint pivotally interconnects the mounting portion and the shin portion and has an hydraulic knee flexion control device and (ii) the ankle joint pivotally interconnects the shin member and the foot member and has an hydraulic ankle flexion control device, and wherein the prosthesis further comprises: a flexion control system for controlling knee and ankle joint flexion and including an hydraulic circuit of which the knee and ankle flexion control devices form part, at least one energy conversion device for converting fluid flow energy in the hydraulic circuit resulting from knee or ankle flexion into mechanical movement and vice versa, and an energy storage element arranged to store energy from the or each energy conversion device and to feed stored energy back to the or each energy conversion device to cause fluid flow in the hydraulic circuit thereby to drive the knee or ankle flexion control device to generate a knee flexion or extension moment or an ankle flexion movement; at least one sensor for sensing a kinetic or kinematic parameter of locomotion; and a processor coupled to the sensor and the flexion control system and arranged to control both the storage of energy associated with fluid flow resulting from knee and ankle flexion as well as the return of energy to the knee and ankle flexion control devices at different respective parts of a walking gait cycle in response to signals received from the sensor or sensors.

According to another aspect of the invention, there is provided a lower limb prosthesis including structural members interconnected by a pivotal joint, which joint includes an hydraulic flexion control device forming part of an hydraulic circuit, wherein the hydraulic circuit further comprises an energy conversion device for converting fluid flow energy into electrical energy and vice-versa, and wherein the prosthesis further comprises a rechargeable battery connected to the energy conversion device via an electrical control circuit, the arrangement of the energy conversion device and the electrical control circuit being such that, in a first part of a walking gait cycle, fluid flow energy generated in the hydraulic circuit by flexion of the joint and operation of the flexion control device is converted to electrical energy which is stored by the battery and such that, in a second part of the gait cycle, electrical energy from the battery is converted to fluid flow energy in the hydraulic circuit which drives the flexion control device so as to generate a flexion moment in the joint. It is preferred that the energy conversion device comprises the combination of a first energy convertor for converting fluid flow energy to mechanical movement and vice versa and a second energy convertor in the form of an electrical machine for converting the mechanical movement to electrical energy and vice versa.

According to yet a further aspect of the invention, a lower limb prosthesis includes structural members interconnected by a pivotal joint, which joint includes an hydraulic flexion control device forming part of an hydraulic circuit, wherein the hydraulic circuit further comprises a pressure accumulator for storing energy resulting from fluid flow in the hydraulic circuit caused by flexion of the joint, and wherein the prosthesis further comprises an electric motor coupled to the pressure accumulator for varying the volume of an hydraulic pressure chamber of the accumulator.

The invention will now be described by way of example with reference to the drawings in which:

FIG. 4 is a table showing functions of the prosthesis of FIG. 2;

Figure 1A:
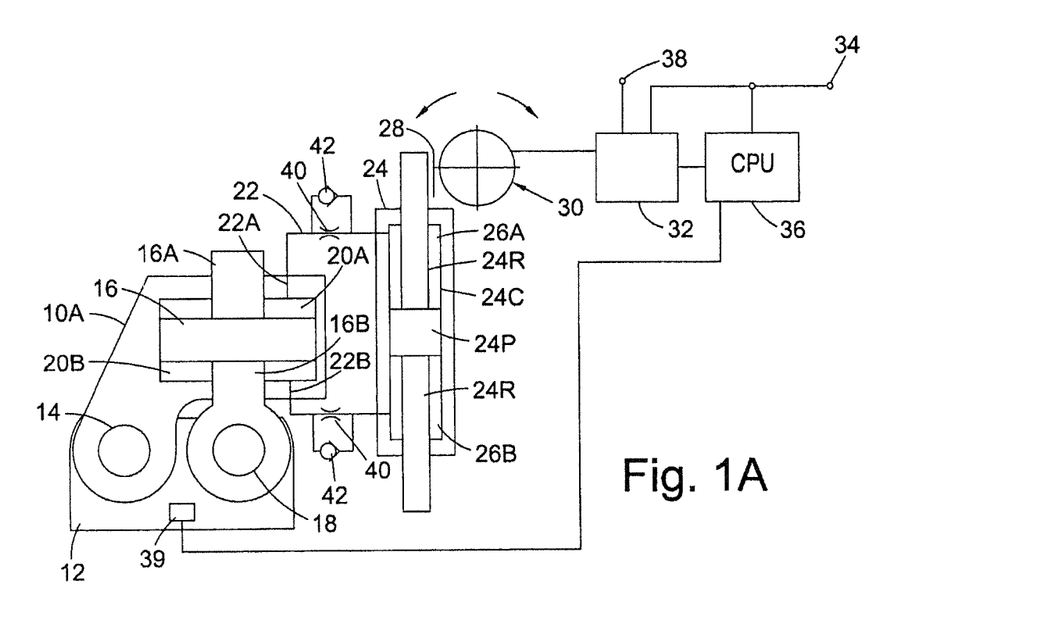
FIG. 1A is a diagrammatic representation of a prosthetic ankle in accordance with the invention.

Referring to FIG. 1A, a prosthetic ankle in accordance with the invention has an ankle joint body 10A constituting a shin component insofar as the ankle joint body 10A is intended to be connected to or form part of a shin member (not shown), and a foot component 12 intended to be connected to or form part of a prosthetic foot (not shown). The ankle joint body 10A is pivotally connected to the foot component 12 by a first pivotal connection 14 defining a medial-lateral ankle joint flexion axis. The ankle joint body 10A also forms the cylinder of an ankle joint piston and cylinder assembly with a superior-inferior central axis, the cylinder housing a piston 16 with upper and lower piston rods 16A, 16B. The lower piston rod 16B is pivotally connected to the foot component 12 at a second pivotal connection 18, this second pivotal connection defining a second medial-lateral axis which is spaced, in this instance, posteriorly from the ankle joint flexion axis defined by the first pivotal connection 14. It will be seen that, as the ankle joint body 10A pivots about the ankle joint flexion axis, the piston 16 moves substantially linearly in the cylinder formed by the ankle joint body.

The cylinder is divided into upper and lower chambers 20A, 20B. These chambers are linked by an hydraulic circuit 22 incorporating passages 22A, 22B in the ankle joint body 10A, and an energy conversion device in the form of a slave piston and cylinder assembly 24 having a piston 24P and piston rods 24R which project beyond the cylinder 24C of the assembly 24.

The slave assembly 24 has first and second fluid-filled chambers 26A, 26B which are connected by the hydraulic circuit 22 to the upper and lower chambers 20A, 20B respectively of the cylinder formed in the ankle joint body 10A so that when the piston 16 in the ankle joint body 10A moves, hydraulic fluid flow in the hydraulic circuit 22 causes the slave piston 24P to move correspondingly, the displacement of the slave piston 24P being several times greater than that of the main piston 16 due to its smaller diameter.

One of the slave piston rods 24R has a gear rack 28 on its side surface. The rack 28 engages a pinion on the shaft of an electrical machine 30. When the slave piston 24P is displaced as a result of movement of the piston 16, the rack 28 on the piston rod 24R drives the electrical machine 30 as a generator, causing current flow through a routing circuit 32 to a battery connection terminal 34.

Conversely, when a suitable voltage is applied at the battery terminal 34 and the routing circuit 32 is appropriately configured, the electrical machine 30 acts as a motor and drives the slave piston 24P via the rack 28 on the piston rod 24R, which in turn drives hydraulic fluid through the hydraulic circuit 22 to urge the piston 16 in one direction or the other, depending on the direction of rotation of the electrical machine 30.

Operation of the electrical components is controlled by a CPU 36 which adjusts the routing circuit 32 so as to cause the electrical machine 30 to charge a rechargeable battery (not shown) connected to the battery connection terminal 34 during selected parts of a walking gait cycle. In other parts of the gait cycle, the CPU causes the routing circuit 32 to feed current from the battery connected to the terminal 34 to cause the ankle to flex in the manner described above.

When the electrical machine 30 is operated as a generator, it can be controlled by the CPU 36 to vary the resistance it presents to movement of the slave piston 24 and, therefore, the hydraulic resistance to flexion of the ankle joint so as to suit the requirements of the amputee at a given time, e.g. according to speed of walking and terrain. Similarly, the CPU 36 is programmed to vary the power transmitted to the ankle joint according to such requirements.

In practice, energy is harvested from the ankle and stored in the battery during an initial part of the stance phase as the ground reaction force transmitted via the heel of the prosthetic foot causes the ankle to plantar-flex. Depending on the speed of walking and the ground inclination, the electrical machine is caused to act as a motor in the middle part of the stance phase, powering the ankle into dorsi-flexion in order to propel the centre of gravity of the amputee forwardly. Towards the end of the stance phase, again depending on the speed of walking and the ground inclination, the CPU causes the electrical machine to act as a motor, on this occasion powering the ankle into plantar flexion to assist with the push-off at the end of the stance phase. Such functions are described in more detail below with reference to FIGS. 2, 3A to 3F and 4. The triggering of these different phases of operation may be based on the direction of toe spring movement, which may be sensed using one of the sensors described above, such as a strain gauge on the toe spring. For example, during the roll over phase, the toe spring is deflected by the load which is applied by the amputee. As the amputee continues to walk the load distribution is transferred off the back foot and the energy stored in a toe spring will be released to assist the ankle to plantar flex. The flexion of the toe spring can be used to determine the phases of locomotion of the user and this movement can be used as a trigger to initiate application of power to the ankle. In addition, the anticipation of this movement can be used to determine the phase of locomotion in order to trigger power application to the ankle joint actuator.

In this embodiment of the invention, the shaft of the electrical machine 30 rotates in an anti-clockwise direction as shown in FIG. 1A when energy is harvested at heel strike and when the ankle is powered into plantar-flexion (e.g. at toe-off). The shaft rotates in the opposite direction when energy delivered to power the ankle is dorsi-flexion, e.g. in mid-stance or to lift the toe during swing.

The routing circuit 32 also has a second input 38 allowing connection of an external electrical power source for charging the battery connected to the battery connection terminal 34.

Mounted on the foot component 12 is an accelerometer 39 coupled to an input of the CPU 36. A second sensor (not shown) coupled to the CPU senses the angle of flexion of the ankle. The CPU 36 uses signals from these sensors to determine kinetic and kinematic parameters of locomotion for controlling operation of the electrical machine 30 via the routing circuit 32. Further sensors, such as strain gauges, may be used to determine parameters of locomotion. For example, a strain gauge can be attached to the toe spring to sense the bending moments in the toe spring. The output of this toe spring can be used to determine the phase of the gait cycle based on the bending moment to which the toe spring is subjected. The knowledge of the phase of the gait cycle can then be used to vary flexion in a joint.

Owing to the ability to recover energy from the prosthetic ankle during walking, energy consumption from the battery 34 to drive the ankle into dorsi-flexion or plantar-flexion is minimised, allowing either use of a smaller battery than the prior designs or longer periods between recharging via the external charging input 38.

The hydraulic circuit 22 includes restrictions 40 and accompanying oppositely-directed non-return valves 42. The restrictions 40 comprise variable orifice-area valves controlled by the CPU 36 to allow passive damping of the piston 16, one restriction 40 operating for dorsi-flexion and the other for plantar-flexion. The preferred use of such restrictions 40 is for a fail-safe mode should electrical power be exhausted.

Figure 1B:
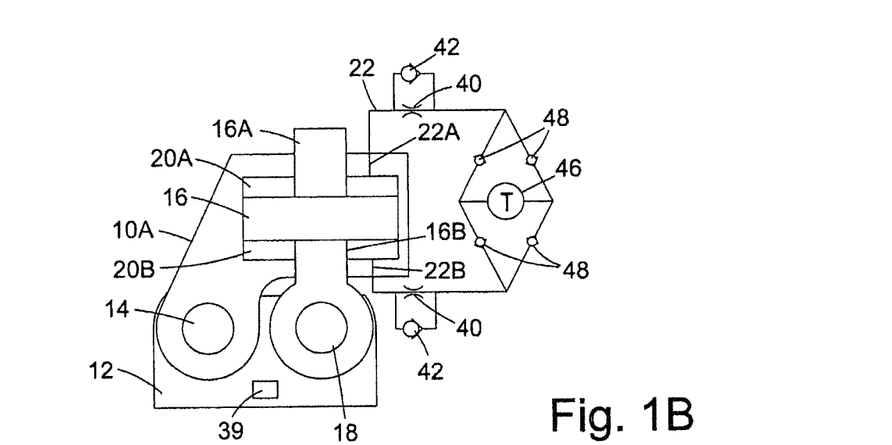
FIG. 1B is a diagrammatic representation of an alternative prosthetic ankle.

Referring to FIG. 1B, in an alternative arrangement for recovering energy from joint flexion produced by walking on the prosthetic ankle, the hydraulic circuit 22 includes a turbine 46 coupled to an electrical generator (not shown) via non-return valves 48 connected in a bridge arrangement. The generator coupled to the turbine 46 is preferably connected in a control circuit similar to that described above with reference to FIG. 1A for charging a rechargeable battery. The non-return valves 48 ensure that the turbine shaft always rotates in the same direction when hydraulic fluid flows around the hydraulic circuit 22 in response to movement of the piston 16 in either direction.

In a further alternative, the turbine 46 is simply connected in the hydraulic circuit 22 and a unidirectional battery charging current is generated by electronic means in the circuitry coupled to an electrical machine associated with the turbine 46.

Figures 2, 2A:
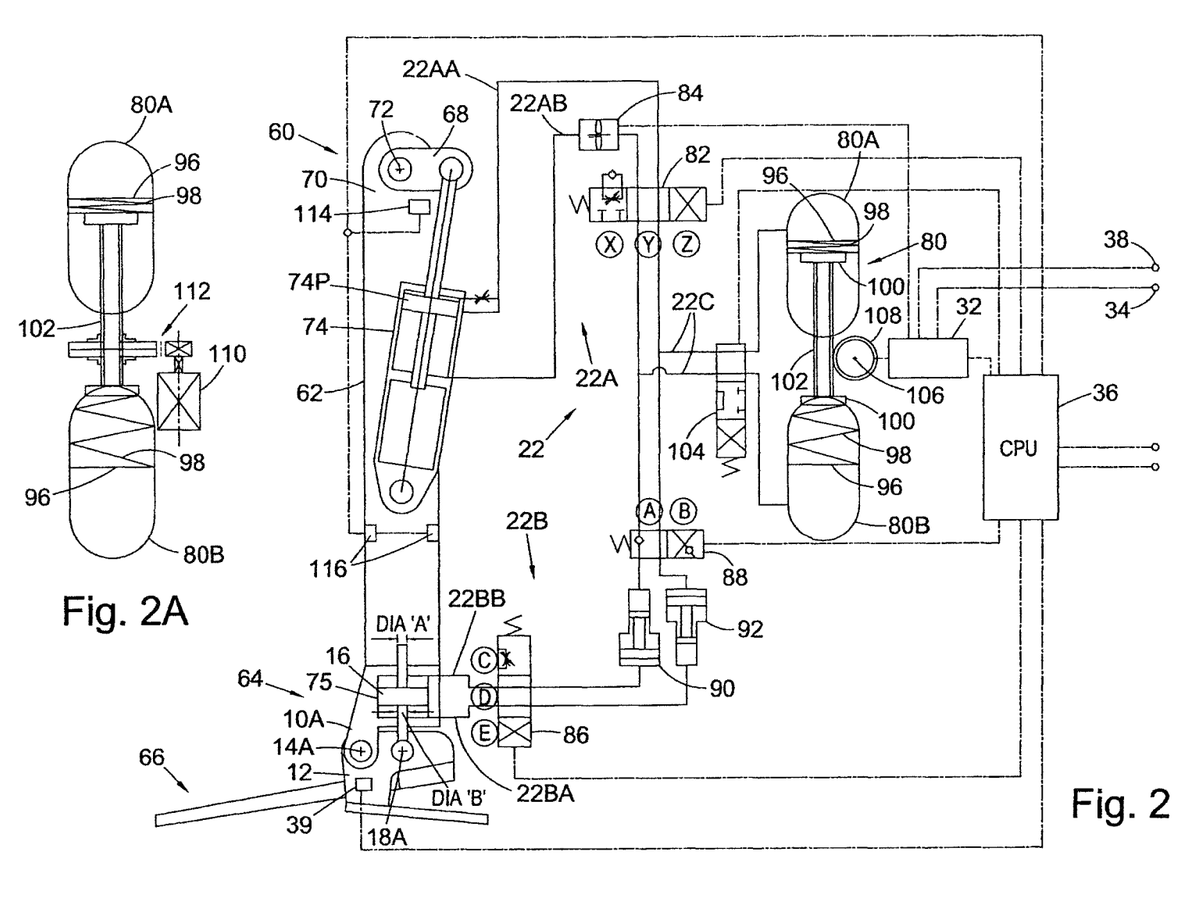
FIG. 2 is a diagrammatic representation of a lower limb prosthesis for a transfemoral amputee.
FIG. 2A is a diagrammatic representation of an alternative accumulator for use in the prosthesis of FIG. 2.

The invention is also applicable to an integrated lower limb prosthesis having a knee joint and an ankle joint, or to a prosthetic knee joint alone. Referring to FIG. 2, an integrated lower limb prosthesis for a transfemoral amputee or an amputee having a through-knee disarticulation has a knee joint 60, a shin member 62, an ankle joint 64 and a foot member 66. The knee joint 60 has an upper component 68 for connection to a limb mounting portion (generally a stump socket) (not shown in FIG. 2). This upper component 68 is pivotally connected to a lower component 70 which, in this case, is an integral part of the shin member 62, to define a knee axis of rotation 72. The knee joint 60 includes an hydraulic knee flexion control device 74 in the form of a piston and cylinder assembly pivotally linking the upper and lower components in known manner so that knee joint flexion (and extension) is controlled by regulating the flow of hydraulic fluid to and from the chambers formed within the control device 74 on opposite sides of a piston 74P within the assembly.

The ankle joint 64 is similar to that described above with reference to FIG. 1A, insofar as it has an ankle joint body 10A rigidly connected to the shin member 62, and pivotally connected to a foot component 12 to define an ankle joint flexion axis 14A. Within the ankle joint body 10A is an ankle flexion control device 75 in the form of a fluid-filled cylinder containing a piston 16 which moves up and down in the cylinder as the ankle joint 64 is flexed. Such movement arises since the piston 16 is pivotally connected to the foot component 12 by a pivot joint having a medial-lateral axis spaced in the anterior-posterior direction with respect to the ankle joint flexion axis 14A, i.e. transversely with respect to the cylinder axis. As before, flexion of the ankle joint is controlled by regulating the flow of hydraulic fluid to and from the chambers on opposite sides of the piston 16.

In this integrated prosthesis, the knee joint 60 and ankle joint 64 share a common hydraulic circuit 22. In effect, the hydraulic circuit 22 has two loops 22A, 22B connected in parallel, both loops being connected by common fluid transfer lines 22C to a twin-pressure-vessel pressure accumulator 80. This pressure accumulator 80 will be described further below.

The hydraulic lines 22AA, 22AB of the first hydraulic loop 22A are connected to chambers on opposite sides of the piston 74P of the knee flexion control device 74. Routing of hydraulic fluid between the knee flexion control device 74 and the fluid transfer lines 22C is controlled by a solenoid-controlled knee control valve 82 in series between the knee flexion control device 74 and the fluid transfer lines 22C. A turbine 84 is connected in one of the knee hydraulic loop lines 22AB.

The hydraulic loop 22B coupling the ankle flexion control device 75 to the fluid transfer lines 22C has first and second ankle control valves 86, 88, both solenoid controlled and separated from each other by first and second hydraulic pressure intensifiers 90, 92. The first ankle flexion control valve 86 has three positions C, D, E and is operable to reverse the connections between hydraulic lines 22BA, 22BB, which communicate with opposite sides of the piston 16, and intensifiers 90, 92, which are oppositely connected. The second ankle flexion control valve 88, coupled between the intensifiers 90, 92 and the fluid transfer lines 22C, has two positions A, B and allows another reversal of connections on the other side of the intensifiers 90, 92 from the first ankle flexion control valve 86.

As shown in FIG. 2, with the valves 86, 88 in positions D and A respectively, when plantar flexion of the foot 66 causes the piston 16 to move upwardly in the ankle joint body 10A, hydraulic fluid pumped through the hydraulic passage 22BB connected to the upper chamber flows to the first intensifier 90 which is oriented so as to increase the resulting hydraulic pressure. The resulting hydraulic fluid flow is transferred to one of the fluid transfer lines 22C via the second valve 88 and, subsequently, to the pressure accumulator 80. When energy is to be stored via the pressure accumulator 80 as a consequence of dorsi-flexion of the ankle, the first ankle flexion control valve 86 is moved to position E so that downward movement of the piston 16 urges fluid through the other hydraulic passage 22BA in the hydraulic loop 22B and thence to the first intensifier 90. The second intensifier 92 intensifies the pressure in fluid flow in the opposite direction, i.e. from the pressure accumulator 80 to the ankle flexion control device 75 to drive the ankle into plantar flexion or dorsi-flexion, as required, the ankle flexion control valves 86, 88 being operated depending on which of the fluid transfer lines 22C carries the fluid pressure to be transferred to the ankle flexion control device. The first intensifier 90 charges the accumulator 80 during plantar-flexion and lifts the toe during the swing phase. The second intensifier 92 is used in powering plantar-flexion after mid-stance. These functions are described in more detail below.

In this embodiment of the invention, there are no pressure intensifiers in the knee hydraulic loop 22A, the knee control valve 82 being the sole control valve between the knee flexion control device 74 and the fluid transfer lines 22C. The function of the knee control valve 82 is similar to that of the first ankle control valve 86 in that it has three positions X, Y, Z and allows reversal and blocking of the lines in the knee loop 22A.

The pressure accumulator 80, in this embodiment, has two linked pressure vessels 80A, 80B each of which has a fluid-filled pressure chamber bounded by a piston 96. Each piston 96 is spring-loaded by a respective spring 98. In each pressure vessel 80A, 80B, the spring 98 is supported by a movable spring base 100 and these spring bases 100 are linked by a shaft 102 so that they move together within their respective pressure vessels 80A, 80B. The arrangement is such that movement of the link 102 to compress the spring 98 in one of the vessels 80A, 80B reduces the compression of the spring 98 in the other vessel 80A, 80B. The position of the shaft 102 as shown in FIG. 2 is such that the spring 98 of a first of the pressure vessels 80A is compressed to a much greater degree than the spring 98 in the second pressure vessel 80B. Accordingly, the fluid pressure in the first pressure vessel 80A is much higher than that in the second pressure vessel 80B. Associated with the accumulator 80 is a three-position accumulator fluid control valve 104. This valve 104 is actuated to reverse the connections depending on the position of the piston rod 102. The blocking position is a charging position.

The fluid pressure in each vessel 80A, 80B depends not only on the position of the shaft 102 but also on the flexion moments in the knee and ankle flexion control devices 74, 75 and on the positions of the control valves 82, 86, 88, 104. Adjustment of the position of the pressure accumulator shaft 102 causes variation in the back pressure experienced in the flexion control devices 74, 75 and thus, varies the resistance to flexion of the knee and ankle joints 60, 64, again dependent on the positions of the control valves 82, 86, 88, 104.

Operation of the flexion control valves 82, 86, 88, together with the fourth control valve 104 in the fluid transfer lines 22C allows pressure energy to be stored in the springs 98 when the prosthesis is loaded at different parts of the walking gait cycle, and such stored energy can be returned via the hydraulic circuit 22 at selected parts of the gait cycle to drive the joints 60, 64 with a view to reducing the energy input required from the amputee and to improve the gait characteristics.

Adjustment of the position of the pressure accumulator shaft 102 is performed by means of a gearbox and electrical machine combination 106, as shown diagrammatically in FIG. 2. The electrical machine of combination 106 is coupled to an electrical routing circuit 32 which has connections to a battery connection terminal 34 and an electrical power input 38.

A CPU 36 controls the routing circuit 32 and the hydraulic solenoid valves 82, 86, 88, 104.

In this embodiment, the gearbox of the gearbox/machine combination 106 is reversible in sense that not only can electrical power be supplied from the routing circuit 32 to drive the electrical machine and, hence, the shaft 102 to compress one or other of the springs 98, but also movement of the shaft 102 can be used to drive the electrical machine as a generator for charging a rechargeable battery connected to the battery connection terminal 34. In this case, the gearbox includes a gear rack cut on the pressure accumulator shaft 102 and a pinion 108 on the shaft of the electrical machine. Additional reduction gearing may be included in the gearbox.

In an alternative arrangement, as shown in FIG. 2A, the pressure accumulator shaft 102 may constitute a worm gear, the shaft 102 being driven to compress one spring 98 or the other by an electric motor 110 and a reduction gearset 112. In a further arrangement forming an embodiment of this invention, no accumulator is used and the joint can be flexed by the use of hydraulic fluid directly driven by the pump.

The programming of the CPU 36 is such that the control valves 82, 86, 88, 104 and the routing circuit 32 are controlled in response to signals received from a plurality of prosthesis-mounted sensors. They comprise a knee angle sensor 114, strain gauges 116 on the shin member 62 for sensing an anterior-posterior shin bending moment, an accelerometer 39 mounted on the foot component 12 and a foot angle sensor (not shown) for measuring the angle of flexion of the ankle joint 64. Each of these sensors is coupled to a respective input port of the CPU 36. Alternatively or additionally, a strain gauge may be used in the toe spring to sense the bending moments in that component.

The sensors referred to above allow, at any given time, determination of where the prosthesis is in the walking gait cycle. Signals from the sensors can also be used to determine ground inclination and kinds of locomotion and different activities as described in, for instance, the above references WO99/08621 and WO2008/103917. Processing of sensor data, including accelerometer outputs, is described in WO2006/024876 and corresponding U.S. patent application Ser. No. 11/661,774, filed 2 March 2007, the disclosure of which is incorporated herein by reference.

Figure 3A:
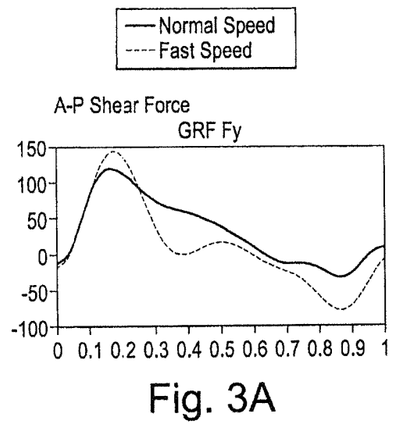
FIGS. 3A to 3F are graphs illustrating the variation of selected locomotion parameters over the course of a walking gait cycle.

The software embodied in the CPU 36 (FIG. 2) may be used to determine, from the sensor outputs, the anterior-posterior shear force, a typical graph for which is illustrated in FIG. 3A. In this graph, variation of the A-P shear force is shown over a single gait cycle at a normal speed of walking (the solid line) and a fast speed of walking (the broken line).

Figure 3B:
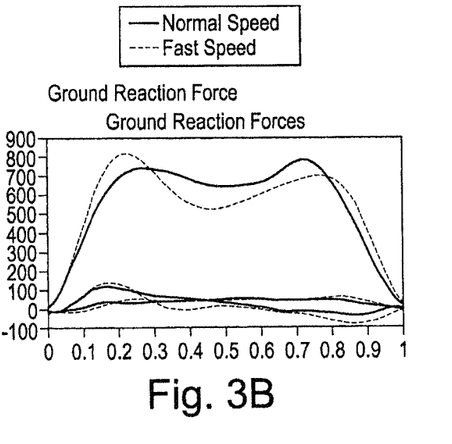

Referring to FIG. 3B, the variation in the ground reaction force, resolved into three components (vertical, anterior-posterior, and medial-lateral) at normal and fast walking speeds is shown.

The output from the knee angle sensor 114 is typically as shown in FIG. 3C, again normalised to a single gait cycle. The shin bending moment, as sensed by strain gauges 116, appears in FIG. 3D. The foot angle (angle flexion) typically follows the curve shown in FIG. 3E and is sensed by sensor 39 (FIG. 2), whilst the foot acceleration is typically as shown in FIG. 3F. In each of FIGS. 3C to 3F the solid line illustrates a typical level walk curve and the dotted line a curve for walking up an incline.

Figure 3C:
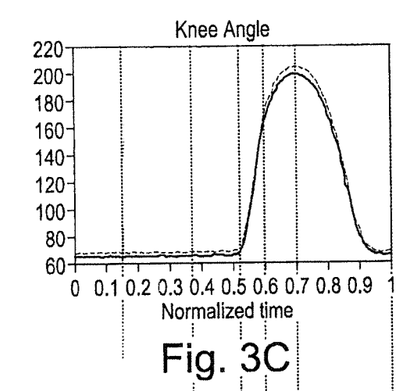
Figure 3D:
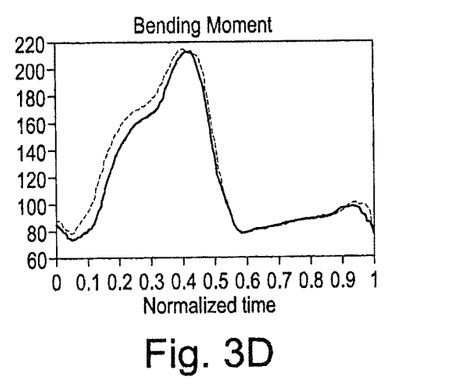
Figure 3E:
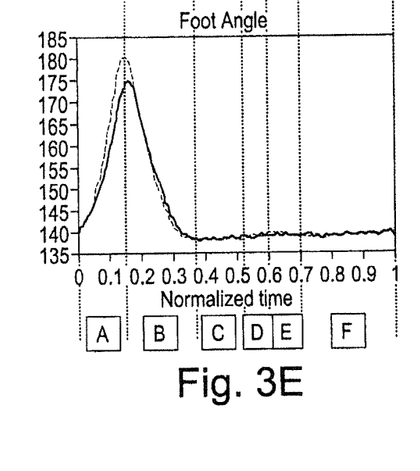
Figure 3F:
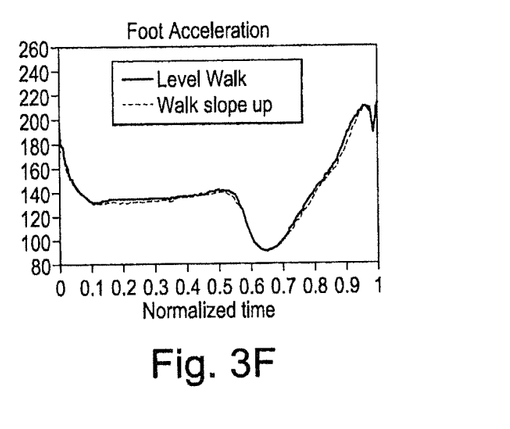

Vertical dotted lines in FIGS. 3C to 3E illustrate the relationships of the sensor outputs with parts of the walking gait cycle, as follows:
A=Initial Stance—increase in foot angle plantar-flexing
B=Mid Stance—start of foot dorsi-flexing
C=Terminal Stance—end of hydraulic movement
D=Initial Swing—initiation of knee flexing
E=Mid Swing—local maxima of knee flexion beginning of extension
F=Terminal Swing These are the start conditions of the relevant gait cycle parts, the letters A to F corresponding to "A" to "F" in FIGS. 3C and 3E.

On the basis of the detected parts of the walking gait phases, as well as on the speed of walking and ground inclination, the CPU controls the operation of the flexion control valves 82, 86, 88, 104 and the gearbox/electrical machine combination 106 (all shown in FIG. 2). Referring to FIG. 4, these elements 82, 86, 88, 104, 106 are operated to recover energy at selected parts of the gait cycle as indicated by the table of FIG. 4. Thus, "ER" or "Er" indicate energy recovery phases in both the ankle joint and the knee joint. At other times, stored energy or externally supplied energy (electrical energy supplied via terminals 34, 38 and energy stored in pressure accumulator springs 98) is used to power flexion of the ankle joint or the knee joint, as indicated by the abbreviation "Pwr". As described above, operation of the gearbox/electrical machine combination 106 under the control of the CPU 36 via the routing circuit 32 can be used to control the resistance to flexion in both joints. Thus, the abbreviations "LD", "MD", and "HD" indicate low resistance, medium resistance and high resistance respectively, according to the part of the gait cycle, the speed of walking, and the ground inclination as shown.

Of particular note are the periods of energy recovery from the ankle joint during the initial stance (regardless of walking speed and ground inclination) and mid-stance (slow walking and down hill) parts of the gait cycle. As to powering the ankle joint, energy is supplied to the joint during mid-stance when walking fast and/or when walking up hill. This is powered dorsi-flexion to assist in driving the centre of gravity of the amputee forwards during the stance phase. In the final part of the stance phase, the ankle joint is driven in plantar-flexion when walking fast or walking up hill to assist with the push-off at the end of the stance phase.

With regard to the knee joint, the limb is adjusted to present a high resistance to knee flexion during initial stance, a degree of yield being allowed for the purpose of recovering energy from the knee joint, as shown in FIG. 4. Energy is also recovered from the knee joint during an initial part of the swing phase and towards the end of the swing phase (the terminal swing part of the swing phase), the prosthesis resisting knee flexion and knee extension respectively. In the mid-stance and terminal stance parts of the stance phase, the knee is powered towards extension and flexion respectively. In addition, in the middle of the swing phase ("mid-swing"), knee extension is assisted when walking fast or walking up hill.

In FIG. 4, the "ankle control" and the "knee control" columns indicate the position of the flexion control valves 82, 86, 88 (FIG. 2). The valve positions are labelled X, Y, Z (valve 82); C, D, E (valve 86); and A, B (valve 88) respectively. Valve positions A and Z are associated with energy recovery, fluid flow energy being fed from the ankle joint and the knee joint respectively to the accumulator 80. In some circumstances, it is preferred to use variable area orifices to provide flexion damping resistance, as represented by position X of the knee flexion control valve 82 and position C of the ankle flexion control valve 86.

The turbine 84 (FIG. 2) can also be used to charge the battery through its link to the routing circuit 32 or can be driven through the same link to increase the hydraulic fluid flow rate in line 22AB.

The ability to power flexion of the ankle joint is also used in this embodiment of the invention to provide active balance control. Referring to FIG. 2, the bending moment sensors 116 or the ankle flexion angle sensor (not shown) can be used to detect body sway when the amputee is standing. The processor is arranged to generate an error signal when data from signals generated by the sensors deviate excessively from a calibrated value. The processor includes a closed loop control system to operate the control valves 86, 88, 104 to apply pressurised fluid to the ankle joint control device 75 so as to actuate the ankle actively to counter the sway. Accordingly, this assistive recovery mechanism actuates the ankle actively in either plantar-flexion when excessive anterior sway (e.g. dorsi-flexion when standing) is detected, or actively in the dorsi-flexion direction if excessive posterior sway (e.g. plantar-flexion when standing) is detected.

Figure 5:
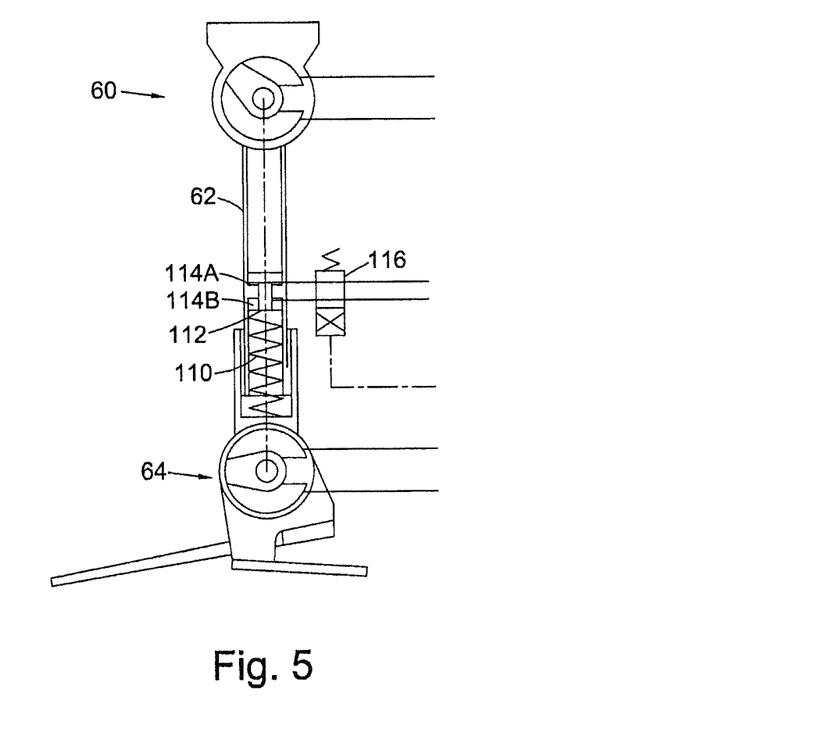
FIG. 5 is a diagrammatic representation of a telescopic shin member.

Referring to FIG. 5, energy may also be recovered in an embodiment having a telescopic shin member 62. In this embodiment, the prosthesis has knee and ankle joints 60, 74 each containing a rotary hydraulic flexion control device coupled to a common hydraulic circuit similar to that shown in FIG. 2. The shin member 62 incorporates, in known manner, a spring 110 to allow the shin parts to reciprocate relative to each other when load is applied and removed from the prosthesis. In this prosthesis, however, the spring acts against an hydraulic piston 112 mounted in one of the shin member parts. The piston encloses, in conjunction with the shin member part, two hydraulic fluid chambers 114A, 114B which are coupled to a control valve 116. This valve 116 is solenoid controlled from the CPU to charge the pressure accumulator and/or a rechargeable battery as described above in conjunction with FIGS. 1, 2 and 4. This occurs at heel strike. Additionally, the processor may be programmed to cause pressurised fluid to be applied to one or other of the hydraulic chambers 114A, 114B to lengthen the shin member 62 at toe-off and/or to shorten it during the swing phase.

Figure 6:
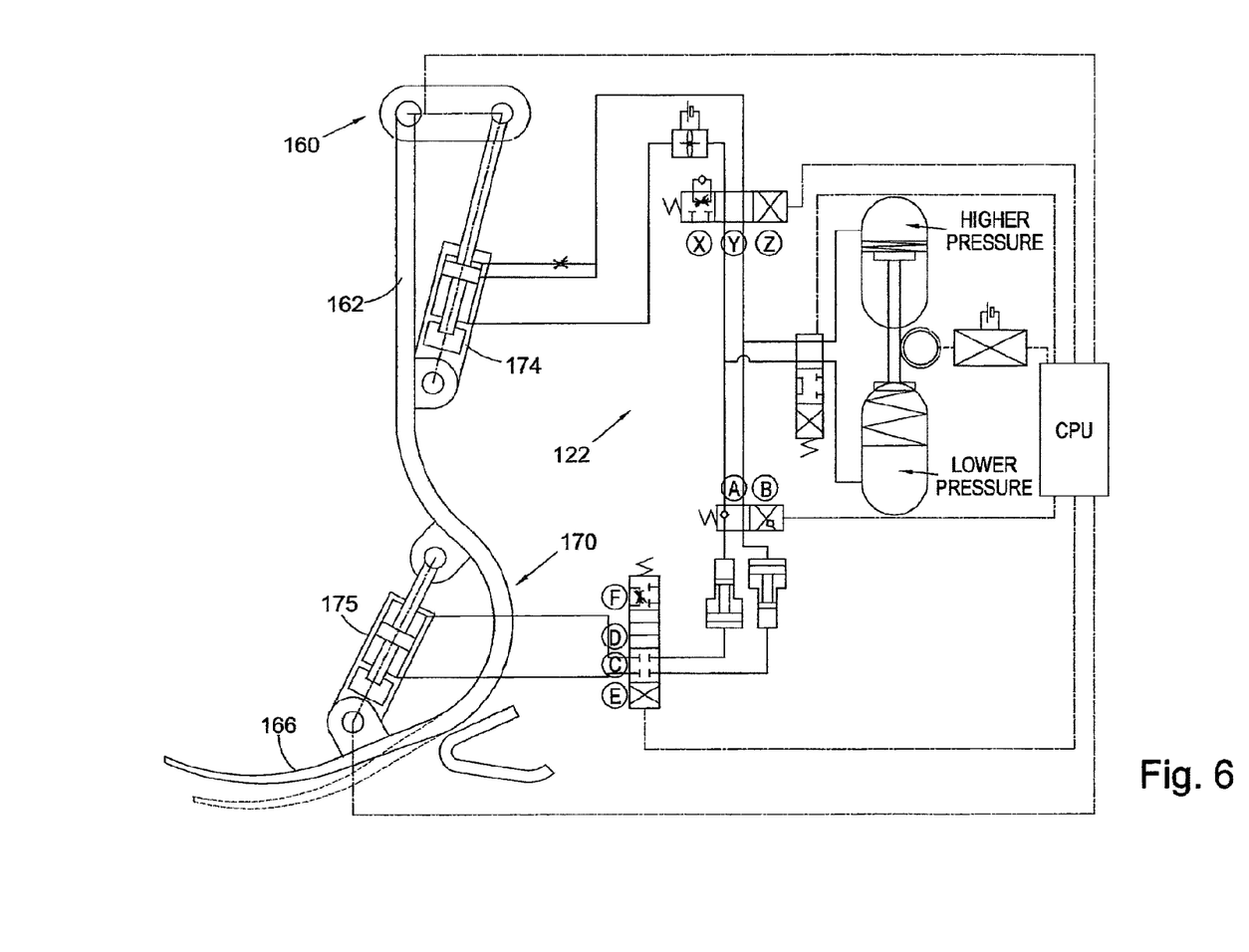
FIG. 6 is a diagrammatic representation of a further lower limb prosthesis in accordance with the invention.

The invention is also applicable to a lower limb prosthesis in which one or more of the structural members is in the form of a resilient blade, as shown in FIG. 6. The prosthesis of FIG. 6 has a monolithic carbon fibre reinforced plastics spring forming a shin member 162 and a foot member 166. The shin member 162 merges into the foot member 166 in an ankle region 170. The blade, as shown in FIG. 6, curves in the ankle region and this curved portion is bridged by an ankle flexion control device 175 in the form of an hydraulic ram pivotally connected at one end to the shin member 162 and at its other end to the foot member 166.

At the knee joint 160, the shin member 162 is connected to an upper limb component 168 by a second hydraulic ram 174 in a manner similar to that described above with reference to FIG. 2.

The flexion control system and its associated hydraulic circuit 122 is similar to that described above with reference to FIG. 2 and operates as follows.

As body weight is loaded on the limb there is a tendency for the elastic/spring elements/structures of the prosthesis to begin to deflect as they strain and thus begin to store mechanical energy. While this loading action is taking place the hydraulic actuators can apply additional compression to the elastic elements. In effect additional elastic energy is transferred to the springs while the spring elements are compressing (under body loading), thus the added energy is applied simultaneously and in series with body loading.

The added elastic energy in the structure can then be advantageously released in the gait cycle, during mid-stance and the later phases of stance phase. For example, energy can be released as heel-rise of the foot begins or during stance-phase knee extension. The degree of additional energy storage is controlled intelligently from the on-board electronics and control system and modulated according to walking speed, terrain and activity mode as well as programmed to individual requirements. The mechanism of energy return can be advantageously applied at any point in the gait cycle when the individual joints are required to extend and timed according to sensed gait phases.

In more detail operation is as follows:

From heel strike to mid stance, high pressure oil flows through valve ports E (FIG. 6) to assist dorsi-flexion and add pre-load the toe spring. Alternatively, there may be an option to charge the accumulator from heel-strike to mid-stance with the valve in position D.

During roll-over in the stance phase, the ankle piston is locked with valve in position C to allow transition to powered mode.

After roll-over toe spring energy is released with the valve in position F, or receives additional power with valve in position D.

During swing the toe may be lifted, if required, for ground clearance with valve in position E.

The invention claimed is:

1. An active ankle joint prosthesis comprising a shin member and a foot member and constructed such that the foot member is able to execute a flexion movement relative to the shin member, and an ankle flexion control system for controlling and actively driving the relative flexion movement between the shin member and the foot member, wherein the ankle flexion control system comprises:

a hydraulic circuit interconnecting the shin member and the foot member, and comprising a piston and cylinder assembly for converting fluid flow energy in the hydraulic circuit into mechanical movement resulting in ankle flexion and for converting the mechanical movement resulting from ankle flexion into fluid flow energy in the hydraulic circuit;

a rechargeable battery;

a generator-motor electrical machine operable as a generator to convert the fluid flow energy in the hydraulic circuit into electrical energy for charging the rechargeable battery and as a motor to convert the electrical energy from the battery into fluid flow energy in the hydraulic circuit; and an energy input coupled to the rechargeable battery and configured to receive energy into the ankle flexion control system from an external energy source to further charge the battery from the said external energy source;

and wherein the active ankle joint prosthesis further comprises;

at least one sensor for sensing a kinetic or kinematic parameter of locomotion; and a processor coupled to the at least one sensor and the ankle flexion control system, and wherein the processor is configured to control both (i) fluid flow energy resulting from flexion movement arising from application of a load to the active ankle joint prosthesis and (ii) delivery of electrical energy to the generator-motor electrical machine to drive the fluid flow energy in the hydraulic circuit and consequently drive mechanical movement in the piston and cylinder assembly resulting in the flexion of the active ankle joint prosthesis at different parts of a walking gait cycle in response to signals received from the at least one sensor, such that, in a part of a stance phase following peak plantar flexion, the ankle flexion control system is configured to drive the foot member in a direction of dorsi-flexion.

2. An active ankle joint prosthesis according to claim 1, wherein the processor is arranged to control the storage of energy in the rechargeable battery associated with fluid flow energy in the hydraulic circuit arising from flexion of the ankle joint prosthesis.

3. An active ankle joint prosthesis according to claim 2, wherein the ankle flexion control system and the processor are arranged such that the fluid flow energy is driven in the hydraulic circuit to result in the ankle joint flexion in at least one further part of the walking gait cycle in addition to the part of the stance phase following peak plantar flexion in response to signals received from the at least one sensor and such that, in the at least one further part of the walking gait cycle, the ankle flexion control system is operated to drive fluid in the hydraulic circuit.

4. An active ankle joint prosthesis according to claim 3, wherein the flexion control system and the processor are arranged such that the at least one further part of the walking gait cycle comprises a final part of the stance phase and such that the ankle flexion control system is driven to urge the foot member in a direction of plantar-flexion in the said stance phase final part.

5. An active ankle joint prosthesis according to claim 1, wherein the generator-motor electrical machine comprises a gear mechanism for converting linear motion to rotary motion.

6. An active ankle joint prosthesis according to claim 1, wherein the generator-motor electrical machine comprises a turbine in the hydraulic circuit.

7. An active ankle joint prosthesis according to claim 1, wherein the processor is coupled to the generator-motor electrical machine and arranged to control its operation thereby to vary the resistance to fluid flow energy in the hydraulic circuit presented by the said piston and cylinder assembly.

8. An active ankle joint prosthesis according to claim 1, wherein at least one of the at least one sensor is operable in conjunction with the processor to detect body sway when in a standing condition, the processor being arranged to cause fluid flow energy in the hydraulic circuit in response to such sway detection so as to apply the ankle joint flexion to the ankle joint prosthesis countering the sway.

9. An active lower limb prosthesis for a transfemoral or through-knee disarticulation amputee comprising a prosthetic knee and the active ankle joint prosthesis according to claim 1, wherein the shin member of the active ankle joint prosthesis is connected to the prosthetic knee, and wherein the prosthetic knee comprises an upper knee component for connection to a residual limb of the amputee, a lower knee component connected to the shin member and pivotally mounted to the upper knee component, and a hydraulic knee flexion control system interconnecting the upper knee component and lower knee component, which hydraulic knee flexion control system is hydraulically connected to said hydraulic circuit of the ankle flexion control system, such that fluid flow energy is created in the hydraulic circuit in response to flexion of the prosthetic knee.

10. An active prosthesis according to claim 9, wherein the ankle flexion control system and the processor are configured to cause the fluid flow energy in the hydraulic circuit resulting from knee flexion to be converted in the said generator-motor electrical machine to the electrical energy, wherein the electrical energy is stored in the rechargeable battery, and wherein the energy stored in the rechargeable battery is configured to be converted back to fluid flow energy and directed to the knee flexion control system to generate knee flexion.

11. An active prosthesis according to claim 10, wherein the ankle flexion control system and the processor are operably connected to the knee flexion control system to cause the knee flexion control system to apply knee flexion in at least one selected part of the walking gait cycle in response to signals received from the at least one sensor and such that, in parts of the walking gait cycle other than the at least one selected part of the walking gait cycle, the knee flexion control system is operated passively to result in fluid flow energy in the hydraulic circuit.

12. An active prosthesis according to claim 11, wherein the ankle flexion control system and the processor are arranged such that the knee flexion control system drives flexion of the lower knee component relative to the upper knee component
   (a) in a direction of knee extension in a mid-stance part of the walking gait cycle stance phase,
   (b) in a direction of the knee flexion in a final part of the walking gait cycle stance phase, and/or
   (c) in the direction of the knee extension in a mid-swing part of a walking gait cycle swing phase.

13. An active prosthesis according to claim 11, wherein the ankle flexion control system and the processor are arranged such that the knee flexion control system operates passively to allow fluid flow energy in the hydraulic circuit to cause energy from the generator-motor electrical machine to be stored in the rechargeable battery
   (a) in an initial part of the walking gait cycle stance phase,
   (b) in an initial part of the walking gait cycle swing phase, and/or
   (c) in a final part of the walking gait cycle swing phase.

14. An active ankle joint prosthesis according to claim 1, wherein the piston and cylinder assembly comprises a piston attached to one of the shin member and the foot member and a cylinder attached to the other of the shin member and the foot member,
   wherein a portion of the piston is disposed within the cylinder,
   wherein the hydraulic circuit comprises at least one hydraulic loop, the hydraulic loop comprising a first hydraulic line portion connected to a first side of the piston within the cylinder and a second hydraulic line portion connected to a second side of the piston within the cylinder,
   wherein the generator-motor electrical machine is configured (1) to drive hydraulic fluid within the hydraulic loop to create the fluid flow energy to cause the piston to move relative to the cylinder and thereby cause the foot member to move relative to the shin member, and (2) to be driven by the fluid flow energy of the hydraulic fluid moving within the hydraulic loop in response to movement of the foot member relative to the shin member causing movement of the piston relative to the cylinder.

15. An active ankle joint prosthesis according to claim 14, wherein the generator-motor electrical machine is disposed remote from a joint between the shin member and the foot member, such that the generator-motor electrical machine cannot directly apply torque between the shin member and the foot member.

16. An active ankle joint prosthesis according to claim 14, the generator-motor electrical machine is connected to a shaft,
   wherein the shaft is connected to the hydraulic loop, wherein the shaft is configured to move relative to the generator-motor electrical machine in response to movement of the hydraulic fluid within the hydraulic loop,
   wherein in an instance in which the generator-motor electrical machine is operable as a generator, the shaft is configured to cause the generator-motor electrical machine to generate the electrical energy in response to movement of the shaft relative to the generator-motor electrical machine, and wherein in an instance in which the generator-motor electrical machine is operable as a motor, the generator-motor electrical machine is configured to cause the shaft to generate the fluid flow energy in response to movement of the shaft relative to the generator-motor electrical machine.

17. An active ankle joint prosthesis according to claim 16, wherein the first hydraulic line portion is fluidically connected to a first pressure vessel, wherein a first piston is disposed at least partially in the first pressure vessel, wherein the second hydraulic line portion is fluidically connected to a second pressure vessel, wherein a second piston is disposed at least partially in the second pressure vessel, wherein the shaft is connected to each of the first piston and the second piston and configured to move with each of the first piston and the second piston.

* * * * *